US012510065B2

(12) United States Patent
Murphy et al.

(10) Patent No.: US 12,510,065 B2
(45) Date of Patent: Dec. 30, 2025

(54) PREDICTIVE TUBE FAILURE DETECTION FOR PUMP

(71) Applicant: Blue-White Industries, Ltd., Huntington Beach, CA (US)

(72) Inventors: Patrick Michael Murphy, Irvine, CA (US); Robert E. Gledhill, III, Huntington Beach, CA (US); Quang Phan, Garden Grove, CA (US); Jonathan Trong Dinh, Westminster, CA (US); John T. Nguyen, Fountain Valley, CA (US)

(73) Assignee: Blue-White Industries, Ltd., Huntington Beach, CA (US)

( * ) Notice: Subject to any disclaimer, the term of this patent is extended or adjusted under 35 U.S.C. 154(b) by 162 days.

(21) Appl. No.: 18/436,915

(22) Filed: Feb. 8, 2024

(65) Prior Publication Data

US 2024/0271612 A1 Aug. 15, 2024

Related U.S. Application Data

(60) Provisional application No. 63/491,710, filed on Mar. 22, 2023, provisional application No. 63/485,191, filed on Feb. 15, 2023.

(51) Int. Cl.
*F04B 43/00* (2006.01)
*F04B 43/12* (2006.01)
(Continued)

(52) U.S. Cl.
CPC .......... *F04B 43/0081* (2013.01); *F04B 43/12* (2013.01); *F04B 49/065* (2013.01); (Continued)

(58) Field of Classification Search
CPC ...... F04B 43/0081; F04B 43/10; F04B 43/12; F04B 43/1238; F04B 49/10; F04B 49/065;
(Continued)

(56) References Cited

U.S. PATENT DOCUMENTS 7,001,153 B2 2/2006 McDowell et al.
7,284,964 B2 10/2007 McDowell et al.
(Continued)

FOREIGN PATENT DOCUMENTS

EP 3546751 A1 * 10/2019 ............ F04B 49/065
WO WO-2012110313 A1 * 8/2012 .............. F04B 43/12

*Primary Examiner* — Charles G Freay
(74) *Attorney, Agent, or Firm* — Knobbe, Martens, Olson & Bear, LLP

(57) ABSTRACT

A pump system can include a tube disposed about a rotor. The rotor can be configured to drive fluid through the tube as the rotor rotates. The tube can be replaceable when the tube fails. The pump system can include a processor configured to determine a predicted number of revolutions of the rotor before the tube fails based on a number n of past tube failure detection (TFD) events. Each past TFD event can have a corresponding $n^{th}$ TFD value based at least in part on the number of revolutions the rotor had rotated before the tube failed. When n=0, the predicted number of revolutions can be set to a putative value, and when n=1, the predicted number of revolutions can be based at least in part on the first TFD value and the putative value.

25 Claims, 5 Drawing Sheets

(51) Int. Cl.

| | |
|---|---|
| ***F04B 49/06*** | (2006.01) |
| ***F04B 49/10*** | (2006.01) |
| ***F04B 51/00*** | (2006.01) |
| *A61M 5/142* | (2006.01) |

(52) U.S. Cl.
CPC .............. *F04B 49/10* (2013.01); *F04B 51/00* (2013.01); *A61M 5/14232* (2013.01); *F04B 43/1238* (2013.01); *F04B 2201/0803* (2013.01); *F04B 2207/703* (2013.01)

(58) Field of Classification Search
CPC .............. F04B 51/00; F04B 2201/0803; F04B 2207/703; A61M 5/14232
See application file for complete search history.

(56) References Cited

U.S. PATENT DOCUMENTS

| | | | |
|---|---|---|---|
| 8,215,931 | B2 | 7/2012 | McDowell et al. |
| 8,418,364 | B2 * | 4/2013 | McDowell .............. B25B 33/00 29/888.021 |
| 8,639,363 | B2 | 1/2014 | Gledhill, III et al. |
| 9,374,024 | B2 | 6/2016 | Nguyen et al. |
| 9,389,109 | B2 | 7/2016 | Gledhill, III et al. |
| 9,777,720 | B2 | 10/2017 | Gledhill, III et al. |
| 9,828,984 | B2 | 11/2017 | Gledhill, III et al. |
| 9,909,579 | B2 | 3/2018 | Gledhill, III et al. |
| 9,996,089 | B2 | 6/2018 | Gledhill, III et al. |
| 10,330,094 | B2 | 6/2019 | Gledhill, III et al. |
| 10,948,320 | B2 | 3/2021 | Gledhill, III et al. |
| 11,131,300 | B2 | 9/2021 | Gledhill, III et al. |
| 11,150,118 | B2 | 10/2021 | Gledhill, III et al. |
| 11,221,004 | B2 | 1/2022 | Gledhill, III et al. |
| 11,261,857 | B2 | 3/2022 | Gledhill, III et al. |
| D959,238 | S | 8/2022 | Nguyen et al. |
| 11,402,248 | B2 | 8/2022 | Gledhill, III et al. |
| 11,485,653 | B2 | 11/2022 | Gledhill, III et al. |
| 11,578,716 | B2 | 2/2023 | Gledhill, III et al. |
| 11,639,863 | B2 | 5/2023 | Nguyen et al. |
| 11,703,362 | B2 | 7/2023 | Nguyen et al. |
| 11,754,065 | B2 | 9/2023 | Nguyen et al. |
| 11,768,092 | B2 | 9/2023 | Gledhill, III et al. |
| 11,768,929 | B2 | 9/2023 | Gledhill, III et al. |
| 11,781,709 | B2 | 10/2023 | Nguyen et al. |
| 11,891,989 | B2 | 2/2024 | Gledhill, III et al. |
| 11,898,546 | B2 | 2/2024 | Gledhill, III et al. |
| 11,939,972 | B2 | 3/2024 | Nguyen et al. |
| D1,030,452 | S | 6/2024 | Nguyen et al. |
| 12,044,354 | B2 | 7/2024 | Nguyen et al. |
| 12,049,887 | B2 | 7/2024 | Nguyen et al. |
| 2010/0005655 | A1 | 1/2010 | Nguyen |
| 2011/0180172 | A1 | 7/2011 | Gledhill, III et al. |
| 2012/0027622 | A1 | 2/2012 | Ashburn |
| 2013/0092704 | A1 | 4/2013 | Tincher et al. |
| 2015/0211509 | A1 | 7/2015 | Gledhill, III et al. |
| 2018/0291886 | A1 | 10/2018 | Gledhill, III et al. |
| 2018/0298891 | A1 | 10/2018 | Gledhill, III et al. |
| 2019/0301444 | A1 | 10/2019 | James et al. |
| 2022/0316463 | A1 | 10/2022 | Gledhill, III et al. |
| 2023/0287881 | A1 | 9/2023 | Murphy et al. |
| 2023/0417582 | A1 | 12/2023 | Nguyen et al. |
| 2024/0003724 | A1 | 1/2024 | Nguyen et al. |
| 2024/0011479 | A1 | 1/2024 | Gledhill, III et al. |
| 2024/0028694 | A1 | 1/2024 | Gledhill, III et al. |
| 2024/0110559 | A1 | 4/2024 | Nguyen et al. |
| 2024/0247959 | A1 | 7/2024 | Gledhill, III et al. |
| 2024/0254983 | A1 | 8/2024 | Nguyen et al. |

* cited by examiner

PREDICTIVE TUBE FAILURE DETECTION FOR PUMP

CROSS-REFERENCE TO RELATED APPLICATIONS

This application claims the benefit of U.S. Provisional Application No. 63/485,191, filed Feb. 15, 2023, and of U.S. Provisional Application No. 63/491,710, filed Mar. 22, 2023. The entire contents of each of the above-identified patent applications are incorporated herein by reference.

BACKGROUND

Field

The present disclosure relates generally to pumps. More particularly, the present disclosure relates to pump systems with predictive tube failure detection and methods of predicting tube failure.

Description of the Related Art

A peristaltic roller pump typically has rollers. The rollers can be spaced apart and mounted on a rotating carrier that moves the rollers in a circle. A length of flexible tubing can be placed between the rollers and a semi-circular wall. In medical applications, the tubing can be a relatively soft and pliable rubber tubing. For relatively high pressure industrial applications, however, the tubing can be exceedingly durable and rigid, albeit flexible under the high pressure of the rollers.

In use, the rollers can rotate in a circular movement and compress the tubing against the wall, squeezing the fluid through the tubing ahead of the rollers. The rollers can be configured to almost completely occlude the tubing, and operate essentially as a positive displacement pump, each passage of a roller through the semicircle pumps volume of the fluid contained in the tubing segment between the rollers.

As a positive displacement pump, relatively high positive pressures (e.g., 125 psi) or low positive pressures (e.g., 10 psi or less) can be generated at the pump outlet. Peristaltic roller pumps are typically driven by a constant speed motor that draws fluid at a substantially constant rate. Over time, the pressures at the pump outlet can wear on the tubing and result in the development of small pinholes in the tubing. If unnoticed, the pinholes can grow and eventually result in failure of the tubing.

Ruptured tubing can lead to internal leakage and the cessation of proper function. When the pump is used to move a corrosive chemical, such as chlorine, internal leakage can be particularly hazardous. As the chemical comes into contact with the pump components, the pump may become irreparably damaged. This is a serious shortcoming because the costs associated with replacement of the pump can be very substantial.

SUMMARY

Tube failure detection (TFD) can be considered a function of a pump to provide an alarm and/or stop operating if chemical is detected in the pump. Typically, a nonadjustable set value (e.g., a value representing the number of revolutions of the rotor) can be entered and an alarm can trigger and/or the pump can stop operating when the value is reached. In various implementations described herein, the pump can be configured to learn the tube failure and tube replacement habits. Based on the habits, the pump can be able to change its alarm timing and/or shut-off timing.

Various implementations provide a pump system. The pump system can include a motor having a drive shaft. The pump system can include a pump head having a housing, a rotor, a tube, and a tube failure detection sensor. The rotor can be disposed within the housing and connectable to the drive shaft so as to be rotatable therewith. The tube can be within the housing and disposed about the rotor. The rotor can be configured to drive fluid through the tube as the rotor rotates. The tube can be replaceable when the tube fails. The tube failure detection sensor can send a signal when the tube failure has occurred. The pump system can also include a processor configured to receive a signal from the tube failure detection sensor and to determine the number of revolutions of the rotor before having received the signal. The processor can further be configured to determine a predicted number of revolutions of the rotor before the tube fails based on a number n of past tube failure detection (TFD) events. Each past TFD event can have a corresponding $n^{th}$ TFD value based at least in part on the number of revolutions the rotor had rotated before the tube failed.

In various implementations, when n=0, the predicted number of revolutions can be set to a putative value, and when n=1, the predicted number of revolutions can be based at least in part on the first TFD value and the putative value.

In certain implementations, when n=2, the predicted number of revolutions can be based at least in part on the second TFD value and the first TFD value.

In various instances, when n=3, the predicted number of revolutions can be based at least in part on the third TFD value, the second TFD value, and the first TFD value.

In certain systems, when n>3, the predicted number of revolutions can be based at least in part on the $n^{th}$ TFD value, the $(n-1)^{th}$ TFD value, and the $(n-2)^{th}$ TFD value.

In some implementations, the putative value can be based at least in part on the maximum tube life.

In some instances, when n=1, the predicted number of revolutions can be based at least in part on the average of the first TFD value and the putative value.

In some instances, when n=1, the predicted number of revolutions can be based at least in part on the average of the first TFD value counted twice and the putative value.

In some implementations, when n=2, the predicted number of revolutions can be based at least in part on the average of the first TFD value counted twice and the second TFD value.

In certain systems, when n>3, the predicted number of revolutions can be based at least in part on the average of the $n^{th}$ TFD value, the $(n-1)^{th}$ TFD value, and the $(n-2)^{th}$ TFD value.

Some systems can further include an alarm configured to warn the user when the number of revolutions approaches the predicted number of revolutions within a threshold percentage. For example, the threshold percentage can be 30% or less, 25% or less, 20% or less, 15% or less, 10% or less, 7% or less, 5% or less, etc.

Some systems can further include a cover sensor and a pump head cover. The cover sensor can be configured to detect opening of the pump head cover.

In some instances, the system can further include a user input interface configured to allow the user to indicate whether the tube failed and/or has been changed.

As an example, when the user indicates the tube failed, the $n^{th}$ TFD value can equal the number of revolutions the rotor had rotated.

As another example, when the user indicates that the tube did not fail but has been changed, the $n^{th}$ TFD value can equal the number of revolutions the rotor had rotated plus an additional percentage. For example, the additional percentage can be 30% or less, 25% or less, 20% or less, 15% or less, 10% or less, 7% or less, 5% or less, etc.

In some instances, when the user indicates the tube failed, the $n^{th}$ TFD value may not be recorded if the number of revolutions the rotor had rotated is not within a threshold percentage of the previous predicted number of revolutions. For example, the threshold percentage can be at least 60%, at least 70%, at least 80%, etc.

In various implementations, a pump system can include a motor having a drive shaft. The pump system can also include a pump head. The pump head can include a housing, a rotor, and a tube. The rotor can be disposed within the housing and connectable to the drive shaft so as to be rotatable therewith. The tube can be within the housing and disposed about the rotor. The rotor can be configured to drive fluid through the tube as the rotor rotates. The tube can be replaceable when the tube fails. The pump system can also include a processor configured to determine a predicted number of revolutions of the rotor before the tube fails based on a number n of past tube failure detection (TFD) events. Each past TFD event can have a corresponding $n^{th}$ TFD value based at least in part on the number of revolutions the rotor had rotated before the tube failed.

In various implementations, when n=0, the predicted number of revolutions can be set to a putative value, and when n=2, the predicted number of revolutions can be based at least in part on the second TFD value and the first TFD value.

In various instances, when n=3, the predicted number of revolutions can be based at least in part on the third TFD value, the second TFD value, and the first TFD value.

In certain systems, when n>3, the predicted number of revolutions can be based at least in part on the $n^{th}$ TFD value, the $(n-1)^{th}$ TFD value, and the $(n-2)^{th}$ TFD value.

Various implementations provide a pump system. The pump system can include a motor having a drive shaft. The pump system can include a pump head having a housing, a rotor, a tube, and a tube failure detection sensor. The rotor can be disposed within the housing and connectable to the drive shaft so as to be rotatable therewith. The tube can be within the housing and disposed about the rotor. The rotor can be configured to drive fluid through the tube as the rotor rotates. The tube can be replaceable when the tube fails. The tube failure detection sensor can send a signal when the tube failure has occurred. The pump system can include a display which configured to display the number of revolutions of the rotor before having received the signal. The pump system can also include a user input device which permits the user to input the number of revolutions of the rotor before having received the signal. The pump system can also include a processor configured to determine a predicted number of revolutions of the rotor before the tube fails based on a number n of past tube failure detection (TFD) events. Each past TFD event can have a corresponding $n^{th}$ INPUT TFD value based at least in part on the input number of revolutions the rotor had rotated before the tube failed.

In various implementations, when n=0, the predicted number of revolutions can be set to a putative value, and when n=1, the predicted number of revolutions can be based at least in part on the first INPUT TFD value and the putative value.

In certain implementations, when n=2, the predicted number of revolutions can be based at least in part on the second INPUT TFD value and the first INPUT TFD value.

In various instances, when n=3, the predicted number of revolutions can be based at least in part on the third INPUT TFD value, the second INPUT TFD value, and the first INPUT TFD value.

In certain systems, when n>3, the predicted number of revolutions can be based at least in part on the $n^{th}$ INPUT TFD value, the $(n-1)^{th}$ INPUT TFD value, and the $(n-2)^{th}$ INPUT TFD value.

BRIEF DESCRIPTION OF THE DRAWINGS

The features disclosed herein are described below with reference to the drawings of some implementations. The illustrated implementations are intended to illustrate, but not to limit the inventions. The drawings contain the following figures.

DETAILED DESCRIPTION

While the present description sets forth specific details of various implementations, it will be appreciated that the description is illustrative only and should not be construed in any way as limiting. Furthermore, various applications of such implementations and modifications thereto, which may occur to those who are skilled in the art, are also encompassed by the general concepts described herein.

Figure 1:
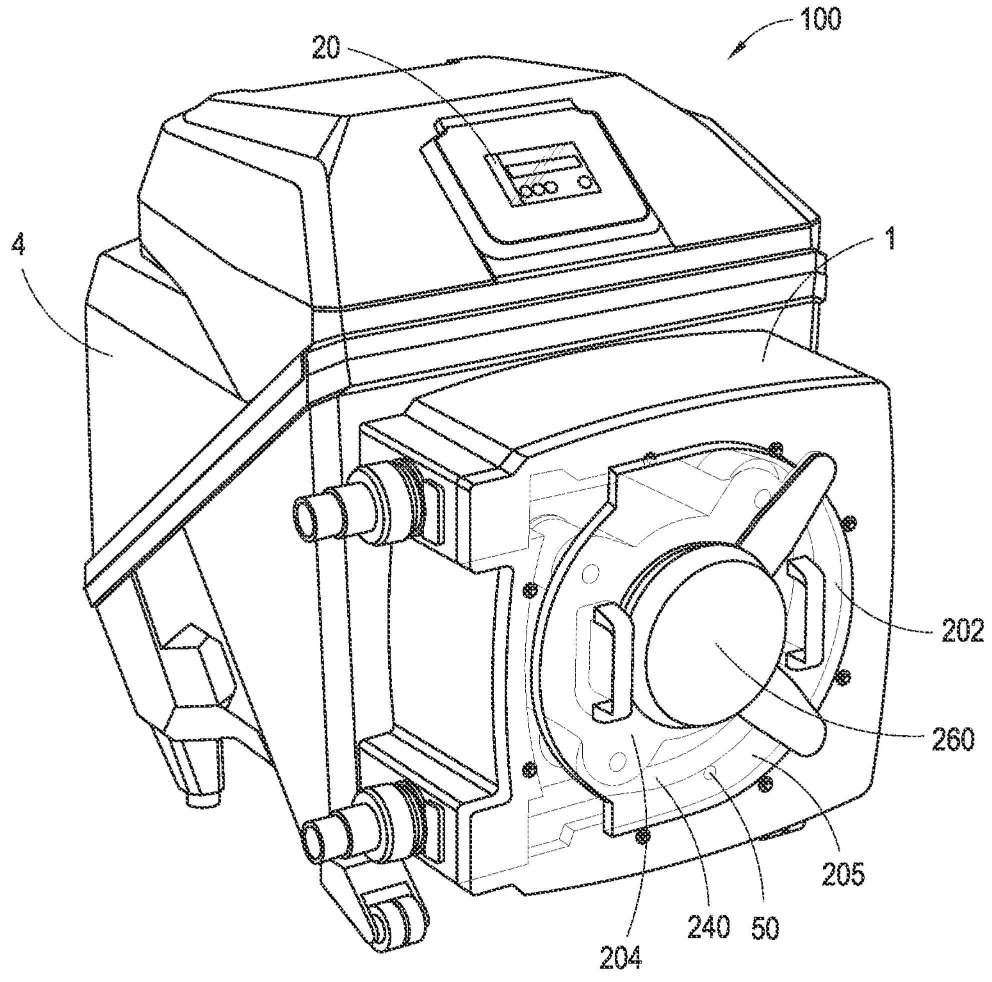
FIG. 1 is a perspective view of an example pump that can have predictive tube failure detection according to various implementations described herein.

As described herein, a pump can have a predictive tube failure detection. FIG. 1 is a perspective view of an example peristaltic pump 100 according to various implementations described herein. The illustrated pump 100 is a peristaltic pump. However, other types of pumps can have predictive tube failure detection as described herein. The example pump 100 has a pump head 1 and a body housing 4.

Figure 2:
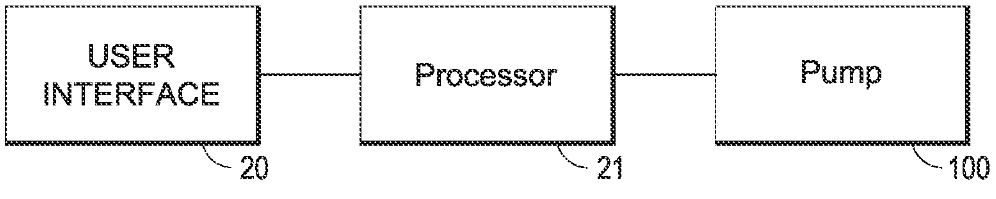
FIG. 2 is a block diagram illustrating an example connection between a user interface in communication with a pump via a processor.

The pump 100 can include a user interface 20 to allow a user to communicate with the pump 100 (e.g., via a processor, such as processing electronics, in communication with the pump 100). In this example, the user interface 20 (and connected processor) is integrated with the pump 100. In other examples, the user interface 20 (and/or connected processor) may be separate from the pump 100. For simplicity, FIG. 2 is a block diagram illustrating an example connection between the user interface 20 in communication with the pump 100 via a processor 21.

Referring back to FIG. 1, the pump 100 can have a pump head 1 that includes a rotor 204 surrounded by a pump head housing 202. The rotor 204 can compress a pump tube or tubing 240 against the pump head housing 202 in a peristaltic squeezing action as the rotor 204 rotates, thereby driving fluid through the pump tube 240. The dimensions of the pump tube 240 and the rotational speed of the rotor 204 can determine the volumetric output of the pump 100. In various implementations, the pump 100 can include a tube failure detection sensor 50 configured to determine when a tube 240 failure has occurred. For example, the tube failure detection sensor 50 can be configured to detect if chemical from the tube 240 leaked into the cavity 205 of the pump head housing 202. In some instances, the tube failure detection sensor 50 can be disposed in the bottom portion of the cavity 205 of the pump head housing 202. In other instances, the tube failure detection sensor 50 can be located in a different area of the pump 100. The tube failure detection sensor 50 can comprise a pump leak monitor as disclosed in U.S. Pat. No. 7,001,153 issued Feb. 21, 2006, entitled PERISTALTIC INJECTOR PUMP LEAK MONITOR, the entirety of the disclosure of which is incorporated herein by reference or as disclosed in U.S. Pat. No. 7,284,964 issued Oct. 23, 2007, entitled PERISTALTIC INJECTOR PUMP LEAK MONITOR, the entirety of the disclosure of which is incorporated herein by reference. The tube failure detection sensor 50 can be configured to send a signal when a tube failure has occurred. As will be described herein, a processor or processing electronics (e.g., within the body housing 4) can be configured to receive the signal from the tube failure detection sensor 50 and determine a predicted number of revolutions of the rotor 204 before the tube 240 fails based on a number of past tube failure detection events.

In various embodiments, the pump 100 can include a motor (e.g., within the body housing 4) to operate the rotor 204. The motor can include a drive shaft and/or axle 260. The rotor 240 can be connectable to the drive shaft and/or axle 260 so as to be rotatable therewith.

Figure 3:
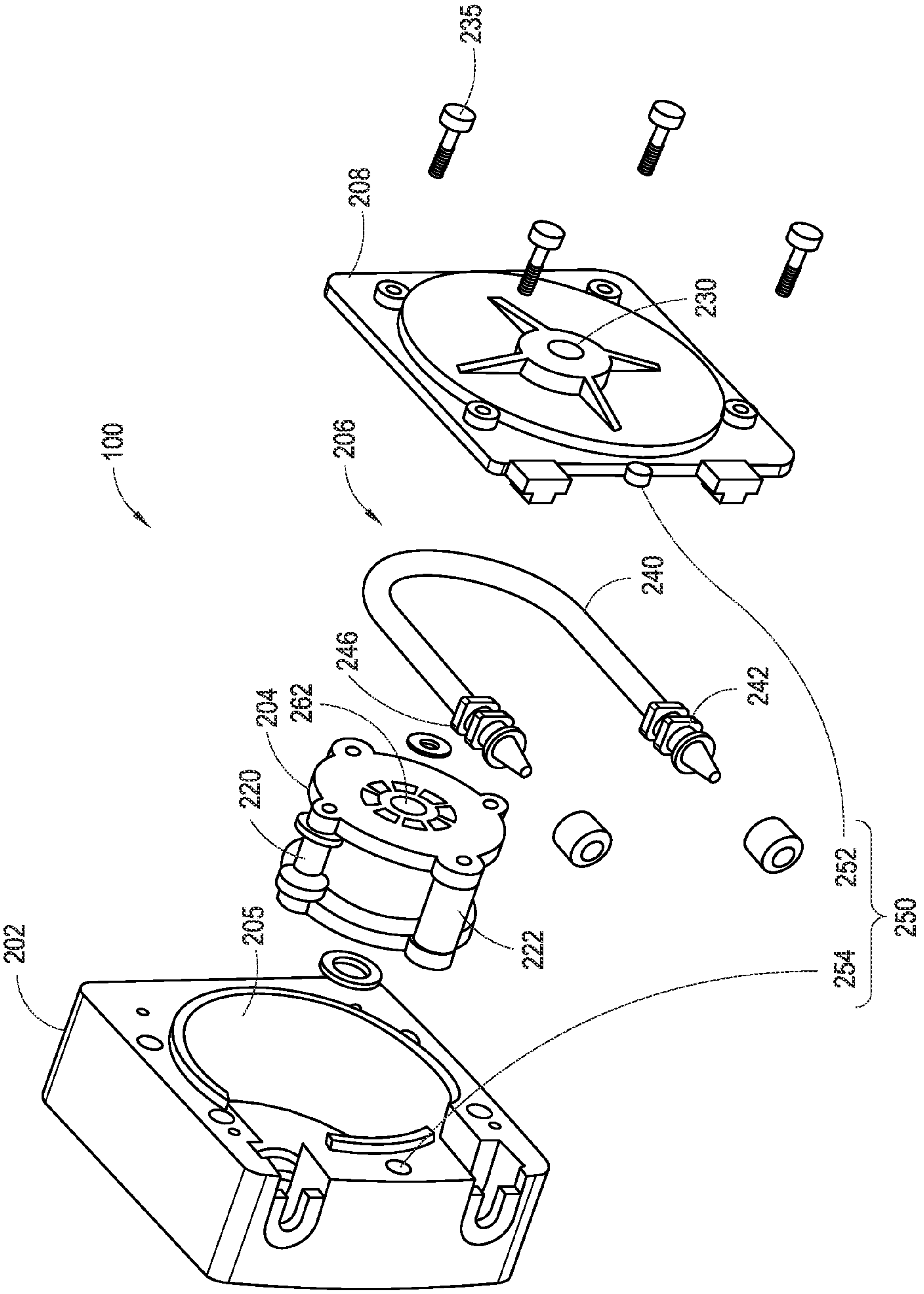
FIG. 3 is an exploded perspective view of components of the pump shown in FIG. 1.

FIG. 3 is an exploded perspective view of components of the pump head 1. As illustrated, the peristaltic pump 100 can comprise a pump head housing 202, a rotor 204 that rotates within a cavity 205 of the pump head housing 202, a tubing assembly 206, and a pump head cover 208 that encloses the rotor 204 and the tubing assembly 206 within the cavity 205 of the pump head housing 202.

As shown in FIG. 3, some embodiments of the pump 100 can be configured such that the head cover 208 of the peristaltic pump 100 comprises an axle support portion 230. The axle support portion 230 can be configured to provide support for an end of the drive shaft and/or axle 260. As such, a drive shaft and/or axle can be disposed through the pump head housing 202, pass through a core or central portion 262 of the rotor 204, and be supported by the axle support portion 230 of the head cover 208. In such an embodiment, when the head cover 208 is mounted on the pump head housing 202, it can support an end of the drive shaft and/or axle which contributes to the longevity and durability of the peristaltic pump 100.

The pump head housing 202 can be formed such that the tubing assembly 206 is positioned in a loop. For example, the tubing assembly 206 can be disposed about the rotor 204 within the pump head housing 202. However, in some embodiments, the pump head housing 202 can be formed such that the tubing assembly 206 passes in a straight line through the pump head housing 202. In other words, the pump head housing 202 can be configured such that the inlet or outlet ports formed therein provide for a loop or straight-line arrangement of the tubing assembly 206 when installed therein.

The tubing assembly 206 can comprise a tube 240 having connectors 242, 246 that are disposed at the opposing ends of the tube 240. It is contemplated that the connectors 242, 246 may be modified and even omitted in some embodiments. The tube 240 and/or tubing assembly 206 can be replaceable when the tube 240 fails (e.g., leaks).

To install the tubing assembly 206, one usually removes the fasteners 235 (e.g., screws) with a tool (e.g., screwdriver) to open the cover 208 and axle support portion 230 to expose the tubing assembly 206. In order to replace the tubing assembly 206, one threads the tubing 240 under the rollers of the rotor 204.

The rotor 204 can comprise a plurality of rollers that compress a tube 240 of the tubing assembly 206 within the pump head housing 202 in order to drive or force fluid through the tube 240 as the rotor 204 rotates. The rotor 204 can rotate in a clockwise or counterclockwise direction. As will be appreciated, fluid in the tube 240 can be urged within the tube 240 along the direction of travel of the rollers.

As shown in FIG. 3, the rollers can comprise at least one alignment roller 220 and at least one compression roller 222. The alignment roller 220 can be formed to comprise a smaller diameter in a central portion thereof and a larger diameter along sides of the alignment roller 220. In this manner, the alignment roller 220 can be configured to maintain the tube 240 within a gap between the rollers and a wall of the pump head housing 202. The unique shape of the alignment roller 220 allows the tube to be urged toward a center of the roller by side edges thereof.

In some embodiments, the compression roller 222 can be configured to compress or pinch the tube 240 against an interior surface of the pump head housing 202 as the compression roller 222 rotates within the pump head housing 202. The compression or pinching of the tube 240 occurs along a length of the tube 240 as the compression roller 222 rotates. The movement and compression urges material disposed within the tube 240 to move through the tube 240 in the direction of rotation of the compression roller 222. Thus, the compression roller 222 can serve to urge fluid or other material through the tube 240 in the direction of the roller's rotation. In use, an industrial peristaltic pump may operate such that the ends of the tube 240 are subjected to high pressures. Additionally, such pumps can also be employed in pumping harmful chemicals.

The pump 100 can further include a cover sensor 250. The cover sensor 250 is shown adjacent the pump head cover 208, but can be disposed in a different location, e.g., within the cavity 205 of the pump head housing 202 or in the body housing 4 of the pump 100.

The cover sensor 250 can be configured to detect opening of the pump head cover 208. As will be described herein, when the cover sensor 250 detects opening of the pump head cover 208, the user can indicate via the user interface 20 whether the tube 240 has or has not been changed due to failure. Such indication can be used for predictive tube failure detection in accordance with various implementations described herein.

In some embodiments, the cover sensor 250 can be integrated with a safety switch mechanism as disclosed in U.S. Pat. No. 8,215,931 issued Jul. 10, 2012, entitled SAFETY SWITCH ON A PERISTALTIC PUMP, the entirety of the disclosure of which is incorporated herein by reference. For example, in prior art peristaltic pumps, the rotor can move at about 125 rpm (if turned "on") or not at all (if turned "off"). However, in order to replace the tubing assembly, one generally must thread the tubing under the rollers of the rotor. Typically, this is attempted in the "off"

mode, when the rotor is not moving at all, and the threading of the tubing is extremely difficult. In an embodiment, it is contemplated that although tubing replacement is easier if the rotor is moving in the "on" mode, serious injury can occur with the rotor moving at about 125 rpm.

Accordingly, in an embodiment, the cover sensor 250 of the peristaltic pump can comprise a safety switch mechanism that causes a peristaltic pump to slow down during use for a given reason. For example, the cover sensor 250 can be configured such that removal of the head cover 208 can cause the peristaltic pump to slow down for maintenance purposes. Thus, an operator may be able to remove the head cover 208 and thread the tubing 240 under slower-moving rollers of the rotor 204 without the danger of a fast-moving rotor.

More specifically, the peristaltic pump can comprise a maintenance mode that is triggered when a head cover 208 is removed. The head cover 208 can comprise a first sensor component 252 that is disposed adjacent to the pump 100 when the head cover 208 is properly fitted onto the pump 100 and is disposed away from the pump 100 when the head cover 208 is removed from the pump 100. The pump 100 can also comprise a second sensor component 254 that is operative to detect whether the first sensor component 252 is disposed adjacent to the pump 100. Further, the second sensor component 254 can be in electrical communication with the pump 100 in order to affect an operational or functional characteristic of the pump 100. In some embodiments, the second sensor component 254 can trigger a reduction in the rotational speed of the rotor 204.

In some embodiments, the first sensor component 252 can comprise a magnet and when the head cover 208 is removed, the second sensor component 254 can detect the absence of the magnet and can trigger the maintenance mode, or slowdown of the rotor 204. However, it is contemplated that other sensor devices can be used other than magnetic-based sensors. For example, it is contemplated that other sensors such as infrared sensors and the like can be used. Once absence of the head cover 208 is detected, the rotor 204 of the peristaltic pump can slow from 125 rpm to 6 rpm. It is contemplated that the second sensor component 254 can be used to trigger other changes in the operation of the pump 100, such as stopping operation of the pump or simply reducing the rotational speed of the rotor 204.

As another example, the second sensor component 254 can send a signal when the pump head cover 208 has been opened. When the processor receives the signal, the pump 100 can allow the user to indicate (e.g., via the user interface 20) whether the tube failed and/or has been changed.

Figure 4:
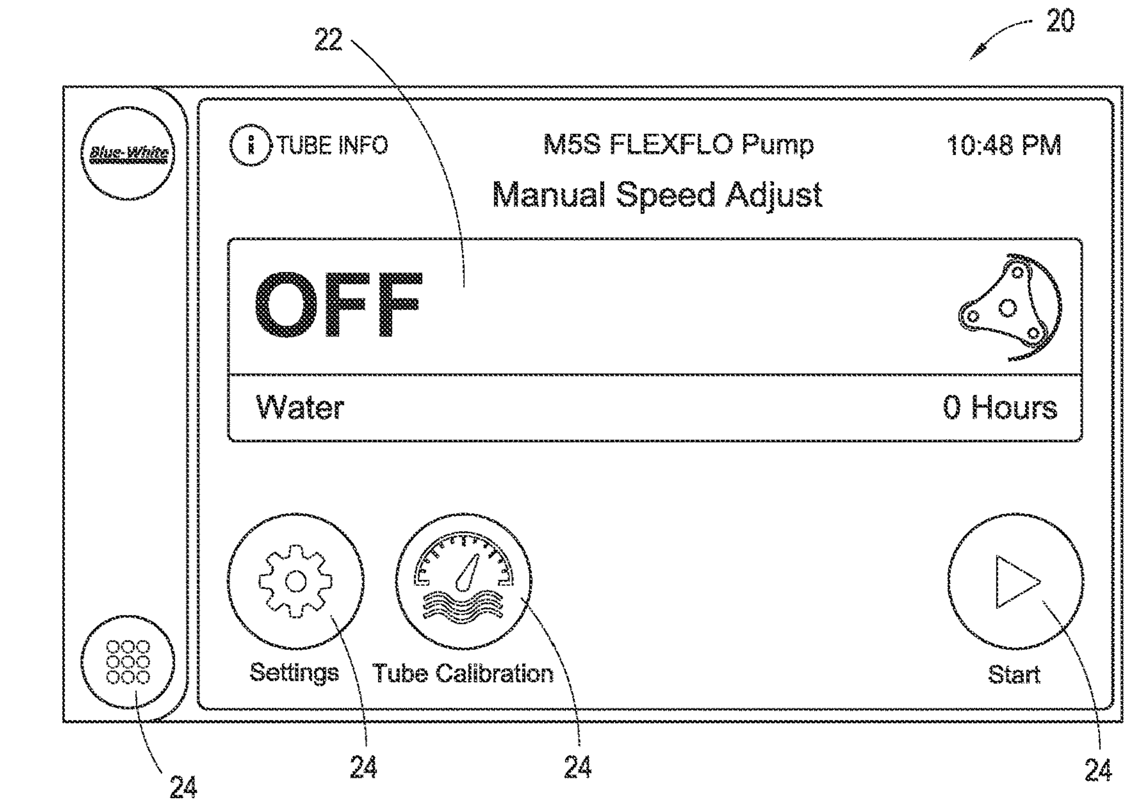
FIG. 4 shows an example user interface according to various implementations described herein.

FIG. 4 shows an example user interface 20. In some implementations, the user interface 20 can include a display 22 (e.g., LCD display, LED display, an OLED display, etc.). The display 22 can present various information and/or operational parameters, for example, pump name, time, tube information, pump status, fluid being pumped, rotation direction, run time, etc.

The user interface 20 can allow the user to control operational parameters of the pump, such as the rotational speed of the rotor via an electronic speed-control system. For example, the user interface 20 can include one or more input stations 24 (e.g., buttons, switches, dials, etc.). In some aspects, the one or more input stations 24 can be arranged as one or more buttons on the display 22 (e.g., one or more buttons on a touch screen display). In some aspects, the one or more input stations 24 can be arranged as a membrane keypad. Other examples are possible. The speed-control system can include a processor, e.g., a microprocessor, configured to receive a command signal from the one or more input stations 24 and transmit a control signal to an electric motor of the pump 100 (which controls the rotor 204) based on the command signal received from the one or more input stations 24. In this way, the speed-control system can allow a user to adjust an operational parameter of the pump 100 through the user interface 20. The processor 21 can include processing electronics. An example processor that can be used include ST's STM32F401 microcontroller. In some instances, it can use an ARM Cortex M4 CPU. The processor can convert an analog signal (e.g., mA) into a digital signal that is processed into a motor revolutions per minute (rpm) at which to run the pump. The processor can perform other functions as well. The main circuit board of the pump 100 can receive the signal inputs from the processor 21 and drive the motor at a determined speed accordingly.

In various implementations, the user interface 20 can access the processor 21 to control the pump 100 local to the pump 100. In various implementations, the pump 100 can additionally or alternatively be controlled at a location remote from the pump 100. For example, the user interface 20 can configure the pump 100 to allow the user to remotely control the pump 100 with incoming signals. In various implementations, the user interface 20 can set one or more input signals for one or more given operational parameters (e.g., motor speed, flow rate, revolutions per minute, etc.).

Figure 5:
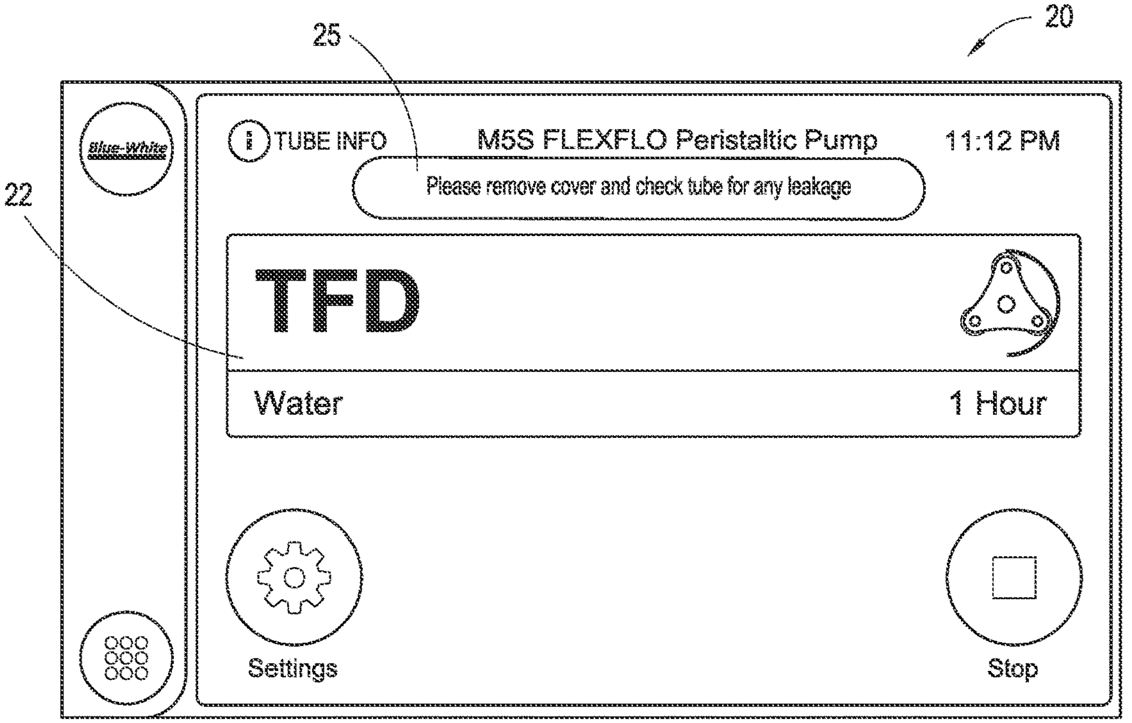
FIG. 5 shows an example user interface 20 with a tube failure detection function.

FIG. 5 shows another example user interface 20 with a tube failure detection (TFD) function. When the tube failure detection sensor 50 detects a possible tube failure, the pump 100 of certain implementations can be configured to stop operating (e.g., stop the rotor from rotating) and/or the user interface 20 can provide to the user a visual warning or alert 25 on the display 22. For example, the user interface 20 can provide a message such as "TFD" on the display 22 and/or recommend the user remove the cover and check tube for any leakage. In various instances, the pump 100 can also provide an audible alert.

Figure 6:
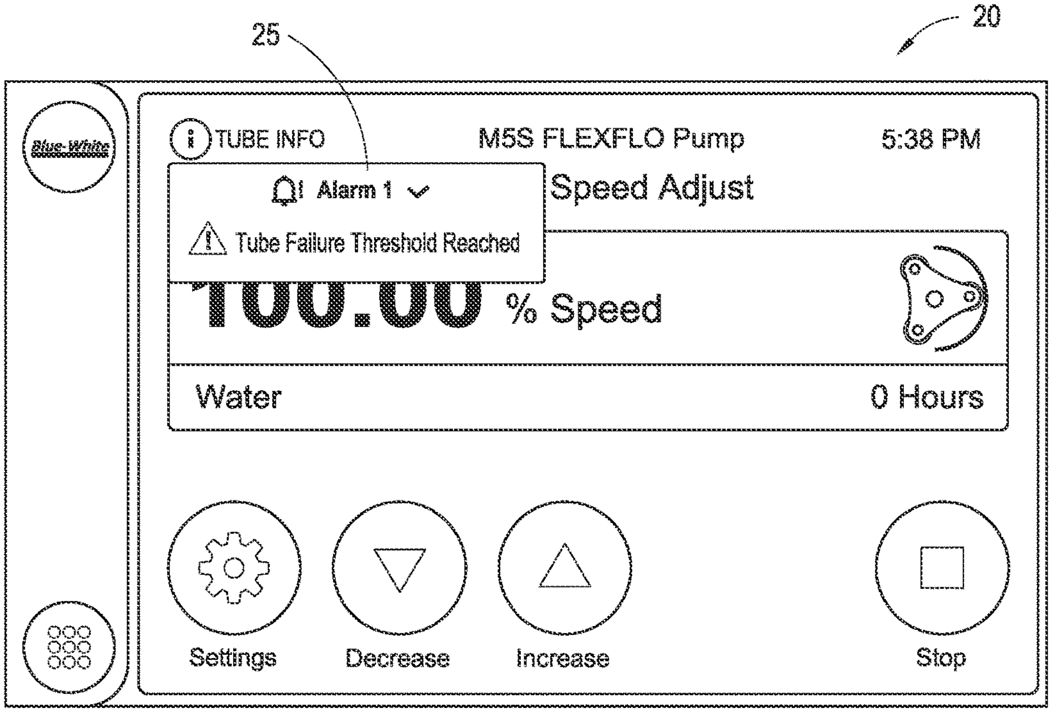
FIG. 6 shows an example user interface 20 with a predictive tube failure detection function.

FIG. 6 shows another example user interface 20 with a predictive tube failure detection function. As shown in FIG. 6, the user interface 20 can provide a predictive TFD function that triggers an alarm 25 (audible and/or visual) to warn the user when the number of revolutions of the rotor approaches the predicted number of revolutions within a threshold percentage (e.g., reaches a predicted revolution threshold). For example, the pump can be configured to store the revolution count of the past TFD events (e.g., the past 1, 2, 3, 4, 5, 6, 7, 8, 9, 10, etc. TFD events). In various implementations, the processor 21 can be configured to receive a signal from the tube failure detection sensor 50 and to determine the number of revolutions of the rotor 204 before having received the signal. The processor 21 further can be configured to determine a predicted number of revolutions of the rotor 204 before the tube 240 fails based on a number of past tube failure detection (TFD) events (e.g., based on the past 1, 2, 3, 4, 5, 6, 7, 8, 9, 10, etc. TFD events). Each past TFD event can have a corresponding TFD value based at least in part on the number of revolutions the rotor 204 had rotated before the tube 240 failed. The pump can be configured to warn the user when the number of revolutions approaches the predicted number of revolutions within a certain percentage or a threshold percentage (e.g., 30% or less, 25% or less, 20% or less, 15% or less, 10% or less, 7% or less, 5% or less, etc.). In some implementations, the pump can be configured to stop operating when the number of revolutions approaches or reaches the predicted number of revolutions.

Figure 7:
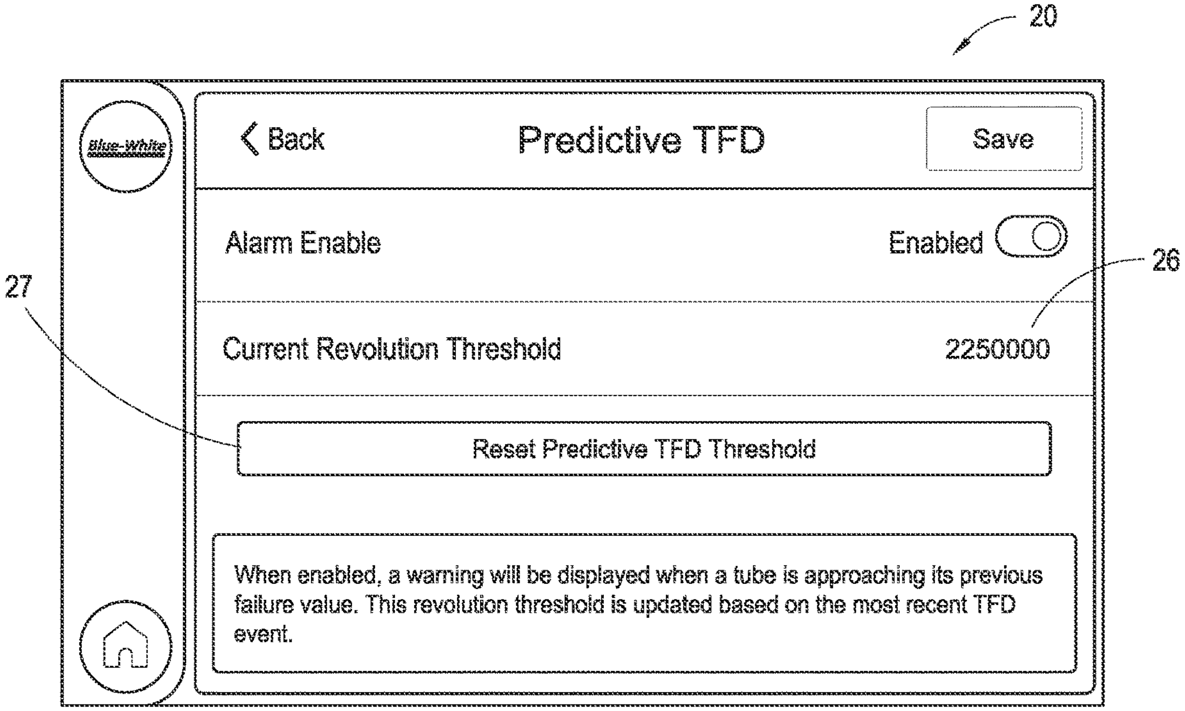
FIG. 7 shows an example user interface 20 with the predictive tube failure detection function enabled.

FIG. 7 shows an example user interface 20 with the predictive TFD function enabled. The user interface 20 can display the current revolution threshold 26 (e.g., the predicted number of revolutions within a threshold percentage). When enabled, a warning can be provided when a tube is approaching its previous failure value. In some implementations, the pump can be configured to stop operating when the tube approaches or reaches its previous failure value. The revolution threshold can be updated based on the most recent TFD event. The pump can also provide the user with an input station 27 to reset the predictive TFD threshold.

Before use, a putative value can be set for the predictive TFD. For example, as an initial set up, the predicted number of revolutions can be set to the putative value. The putative value can be based at least in part on the maximum tube life. In various instances, the putative value for the predictive TFD can be initially set to the default maximum tube life, e.g., 2,250,000 or 2,300,000 revolutions. The processor can be configured to keep track of the number of revolutions of the rotor. An alarm can trigger when the number of revolutions approaches the putative value (e.g., within a certain percentage).

With a first TFD event, the predicted number of revolutions can be based at least in part on the first TFD value and the putative value. For example, the predicted number of revolutions can be based at least in part on the average of the first TFD value and the putative value.

In some instances, the first TFD event can be weighted heavier compared to the putative value. As an example, for a sample size of 3, the predicted number of revolutions can be based at least in part on the average of the first TFD value counted twice and the putative value. For example, if the very first TFD event triggers at 2,100,000 revolutions, and the putative value is 2,300,000, the predicted TFD can be 2,166,666 [e.g., (2,100,000+2,100,000+2,300,000)/3].

The sample size or the stored TFD values can employ a first in first out (FIFO) queue model. For example, when the newest value is added, then the oldest value can be removed. With a second TFD event, the predicted number of revolutions can be based at least in part on the second TFD value and the first TFD value. For a sample size of 3, the putative value can be removed. In some instances, the first TFD event can be weighted heavier compared to a subsequent TFD event. As an example, for a sample size of 3, if the second TFD event triggers at 2,000,000 revolutions, the predicted TFD can be 2,066,666 [e.g., (2,000,000+2,100,000+2,100,000)/3=2,066,666]. In this example, the predicted number of revolutions is based at least in part on the average of the first TFD value counted twice and the second TFD value.

With a third TFD event, the predicted number of revolutions can be based at least in part on the third TFD value, the second TFD value, and the first TFD value. For a sample size of 3, the duplicated first TFD value can be removed. As an example, for a sample size of 3, if the third TFD event triggers at 2,050,000 revolutions, the predicted TFD can be 2,050,000 [e.g., (2,050,000+2,000,000+2,100,000)/3=2,050,000]. In this example, the predicted number of revolutions is based at least in part on the average of the third TFD value, the second TFD value, and the first TFD value.

For n number of past TFD events, each past TFD event can have a corresponding $n^{th}$ TFD value based at least in part on the number of revolutions the rotor had rotated before the tube failed. When n is equal to or greater than 3, the predicted number of revolutions can be based at least in part on the $n^{th}$ TFD value, the $(n-1)^{th}$ TFD value, and the $(n-2)^{th}$ TFD value. For example, the predicted number of revolutions can be based at least in part on the average of the $n^{th}$ TFD value, the $(n-1)^{th}$ TFD value, and the $(n-2)^{th}$ TFD value.

In various instances, the tube 240 may be replaced early or before failure. Predictive TFD can be configured to account for when a tube 240 is replaced early. For example, if a tube 240 replacement occurs before tube failure detection, the pump 100 can be configured to record the current revolution value plus an additional percentage (e.g., 30% or less, 25% or less, 20% or less, 15% or less, 10% or less, 7% or less, 5% or less, etc.). As an example, an operator can replace the tube 240 that ran for 2,150,000 revolutions. The TFD value can be saved as 2,257,500 [e.g., 2,150,000*1.05=2,257,500] in the predictive TFD array.

Although the examples herein determine the predictive TFD based on the past three TFD values (e.g., a sample size of 3), the predictive TFD can be determined based on a different number of past TFD values (e.g., a sample size other than 3). For example, instead of determining the predictive TFD based on the past 3 TFD values, the pump 100 can be configured to determine the predictive TFD based on the past 4, 5, 6, 7, 8, 9, 10, etc. TFD values. As an example, the predicted number of revolutions can be based at least in part on the average of the past 4, 5, 6, 7, 8, 9, 10, etc. TFD values.

In certain embodiments, when the sensor detects opening of the pump head cover 208, the user input interface 20 can be configured to allow the user to indicate whether the tube failed and/or has been changed. When the user indicates the tube failed, the $n^{th}$ TFD value can equal the number of revolutions the rotor had rotated. When the user indicates that the tube did not fail but has been changed, the $n^{th}$ TFD value can equal the number of revolutions the rotor had rotated plus an additional percentage (e.g., 5%).

In various instances, anomalies can occur. Predictive TFD can be configured to account for anomalies. Some values may only be recorded if they are within a certain percentage (e.g., at least 60%, at least 70%, at least 80%, etc.) of the current TFD. For example, when the user indicates the tube failed, the $n^{th}$ TFD value may not be recorded if the number of revolutions the rotor had rotated is not within a threshold percentage (e.g., at least 60%) of the previous predicted number of revolutions.

In some instances, the processor can keep track of the number of revolutions. In some instances, the display can be configured to display the number of revolutions of the rotor before having received the signal from the sensor and the user input device can permit the user to input the number of revolutions of the rotor before having received the signal. Accordingly, the TFD value can be an inputted or INPUT TFD value.

Figure 8:
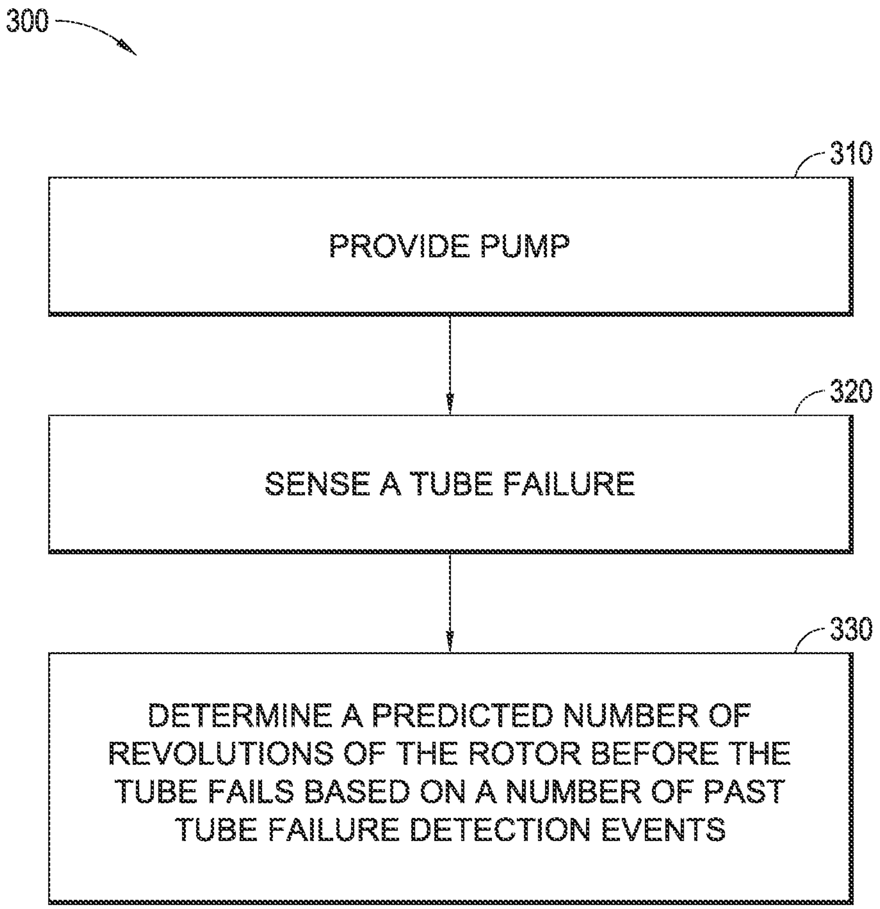
FIG. 8 is a flowchart of an example method of predicting tube failure of a pump system.

FIG. 8 shows a flowchart of an example method of predicting tube failure of a pump system. The method 300 can include providing a pump, as shown in block 310. As described herein, the pump can be a peristaltic pump as shown in FIGS. 1 and 3 or other type of pump. The pump can include a tube disposed about a rotor, wherein the rotor is configured to drive fluid through the tube as the rotor rotates. The tube can be replaceable when the tube fails. The method 300 can include sensing a tube failure as shown in block 320, and determining a predicted number of revolutions of the rotor before the tube fails based on a number n of past TFD events as shown in block 330. As described herein, each TFD event can have a corresponding $n^{th}$ TFD value based at least in part on the number of revolutions the rotor had rotated before the tube failed. When n=0, the predicted number of revolutions can be set to a putative value. When n=1, the predicted number of revolutions can be based at least in part on the first TFD value and the putative value.

In some instances, when n=2, the predicted number of revolutions can be based at least in part on the second TFD value and the first TFD value. In some instances, when n is greater than or equal to 3, the predicted number of revolutions is based at least in part on the $n^{th}$ TFD value, the $(n-1)^{th}$ TFD value, and the $(n-2)^{th}$ TFD value.

In various implementations, the processor can be configured to perform any one or more of the method steps described herein to predict the number of revolutions of the rotor before the tube fails. In various instances, the processor can be configured to execute one or more software applications, e.g., one or more software applications on a computer-readable medium.

Various implementations can be able to self adjust and warn a user before an actual TFD has occurred. In some implementations, the pump can turn off before an actual TFD has occurred. Various such implementations can reduce the risk of chemical spill by preventing or reducing the chance of tube failure. In certain embodiments, pump learning can occur instead of relying on a static value.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A pump system comprising:
a motor having a drive shaft;
a pump head comprising:
 a housing;
 a rotor disposed within the housing and connectable to the drive shaft so as to be rotatable therewith;
 a tube within the housing and disposed about the rotor, wherein the rotor is configured to drive fluid through the tube as the rotor rotates, wherein the tube is replaceable when the tube fails; and
 a tube failure detection sensor, which sends a signal when a tube failure has occurred; and
a processor which is configured to receive a signal from the tube failure detection sensor and to determine the number of revolutions of the rotor before having received the signal, the processor further configured to determine a predicted number of revolutions of the rotor before the tube fails based on a number n of past tube failure detection (TFD) events, each past TFD event having a corresponding $n^{th}$ TFD value based at least in part on the number of revolutions the rotor had rotated before the tube failed, wherein:
 when n=0, the predicted number of revolutions is set to a putative value, and
 when n=1, the predicted number of revolutions is based at least in part on the first TFD value and the putative value.

2. The system of claim 1, wherein when n=2, the predicted number of revolutions is based at least in part on the second TFD value and the first TFD value.

3. The system of claim 2, wherein when n=3, the predicted number of revolutions is based at least in part on the third TFD value, the second TFD value, and the first TFD value.

4. The system of claim 3, wherein when n>3, the predicted number of revolutions is based at least in part on the $n^{th}$ TFD value, the $(n-1)^{th}$ TFD value, and the $(n-2)^{th}$ TFD value.

5. The system of claim 1, wherein the putative value is based at least in part on the maximum tube life.

6. The system of claim 1, wherein when n=1, the predicted number of revolutions is based at least in part on the average of the first TFD value and the putative value.

7. The system of claim 1, wherein when n=1, the predicted number of revolutions is based at least in part on the average of the first TFD value counted twice and the putative value.

8. The system of claim 2, wherein when n=2, the predicted number of revolutions is based at least in part on the average of the first TFD value counted twice and the second TFD value.

9. The system of claim 4, wherein when n>3, the predicted number of revolutions is based at least in part on the average of the $n^{th}$ TFD value, the $(n-1)^{th}$ TFD value, and the $(n-2)^{th}$ TFD value.

10. The system of claim 1, further comprising an alarm configured to warn the user when the number of revolutions approaches the predicted number of revolutions within a threshold percentage.

11. The system of claim 10, wherein the threshold percentage is 5% or less.

12. The system of claim 1, further comprising a cover sensor and a pump head cover, wherein the cover sensor is configured to detect opening of the pump head cover.

13. The system of claim 12, further comprising a user input interface configured to allow the user to indicate whether the tube failed and/or has been changed.

14. The system of claim 13, wherein when the user indicates the tube failed, the $n^{th}$ TFD value equals the number of revolutions the rotor had rotated.

15. The system of claim 13, wherein when the user indicates that the tube did not fail but has been changed, the $n^{th}$ TFD value equals the number of revolutions the rotor had rotated plus an additional percentage.

16. The system of claim 15, wherein the additional percentage is 5% or less.

17. The system of claim 13, wherein when the user indicates the tube failed, the $n^{th}$ TFD value is not recorded if the number of revolutions the rotor had rotated is not within a threshold percentage of the previous predicted number of revolutions.

18. The system of claim 17, wherein the threshold percentage is at least 60%.

19. A pump system comprising:
a motor having a drive shaft;
a pump head comprising:
 a housing;
 a rotor disposed within the housing and connectable to the drive shaft so as to be rotatable therewith; and a tube within the housing and disposed about the rotor, wherein the rotor is configured to drive fluid through the tube as the rotor rotates, wherein the tube is replaceable when the tube fails; and a processor configured to determine a predicted number of revolutions of the rotor before the tube fails based on a number n of past tube failure detection (TFD) events, each past TFD event having a corresponding $n^{th}$ TFD value based at least in part on the number of revolutions the rotor had rotated before the tube failed, wherein:

when n=0, the predicted number of revolutions is set to a putative value, and when n=2, the predicted number of revolutions is based at least in part on the second TFD value and the first TFD value.

20. The system of claim 19, wherein when n=3, the predicted number of revolutions is based at least in part on the third TFD value, the second TFD value, and the first TFD value.

21. The system of claim 20, wherein when n>3, the predicted number of revolutions is based at least in part on the $n^{th}$ TFD value, the $(n-1)^{th}$ TFD value, and the $(n-2)^{th}$ TFD value.

22. A pump system comprising:

a motor having a drive shaft;

a pump head comprising:

a housing;

a rotor disposed within the housing and connectable to the drive shaft so as to be rotatable therewith;

a tube within the housing and disposed about the rotor, wherein the rotor is configured to drive fluid through the tube as the rotor rotates, wherein the tube is replaceable when the tube fails; and a tube failure detection sensor, which sends a signal when a tube failure has occurred;

a display which is configured to display the number of revolutions of the rotor before having received the signal;

a user input device which permits the user to input the number of revolutions of the rotor before having received the signal; and a processor configured to determine a predicted number of revolutions of the rotor before the tube fails based on a number n of past tube failure detection (TFD) events, each past TFD event having a corresponding $n^{th}$ INPUT TFD value based at least in part on the input number of revolutions the rotor had rotated before the tube failed, wherein:

when n=0, the predicted number of revolutions is set to a putative value, and when n=1, the predicted number of revolutions is based at least in part on the first INPUT TFD value and the putative value.

23. The system of claim 22, wherein when n=2, the predicted number of revolutions is based at least in part on the second INPUT TFD value and the first INPUT TFD value.

24. The system of claim 23, wherein when n=3, the predicted number of revolutions is based at least in part on the third INPUT TFD value, the second INPUT TFD value, and the first INPUT TFD value.

25. The system of claim 24, wherein when n>3, the predicted number of revolutions is based at least in part on the $n^{th}$ INPUT TFD value, the $(n-1)^{th}$ INPUT TFD value, and the $(n-2)^{th}$ INPUT TFD value.

* * * * *